(12) United States Patent
Parker

(10) Patent No.: US 6,309,216 B1
(45) Date of Patent: Oct. 30, 2001

(54) CURING SYSTEM FOR PHOTOHARDENABLE MATERIALS

(75) Inventor: William S. Parker, Ann Arbor, MI (US)

(73) Assignee: American Medical Technologies, Inc., Corpus Christi, TX (US)

( * ) Notice: Subject to any disclaimer, the term of this patent is extended or adjusted under 35 U.S.C. 154(b) by 0 days.

(21) Appl. No.: 09/399,889

(22) Filed: Sep. 21, 1999

Related U.S. Application Data

(63) Continuation-in-part of application No. 08/285,907, filed on Aug. 4, 1994.

(51) Int. Cl.⁷ .............................. A61C 13/15; B01J 19/08
(52) U.S. Cl. ...................... 433/29; 250/205; 250/504 H; 315/291; 315/307; 315/360
(58) Field of Search .................. 433/29, 82, 88, 433/142, 215, 226, 229; 250/205, 504 H; 315/156–159, 224, 291, 307, 360

(56) References Cited

U.S. PATENT DOCUMENTS

| | | | |
|---|---|---|---|
| 3,634,938 | 1/1972 | Hutchinson | 433/29 |
| 4,229,658 | 10/1980 | Gonser | 250/504 |
| 4,477,252 | 10/1984 | Lieb et al. | 433/29 |
| 4,661,070 | 4/1987 | Friedman | 433/215 |
| 4,677,287 | 6/1987 | Ejima | 250/205 |
| 4,711,630 | 12/1987 | Durr | 433/29 |
| 4,734,914 | 3/1988 | Yoshikawa | 250/205 |
| 4,839,566 | 6/1989 | Herold et al. | 31/308 |
| 4,948,215 | 8/1990 | Friedman | 433/229 |
| 4,957,441 | 9/1990 | Bryan | 433/228.1 |
| 5,035,621 | 7/1991 | Gottschalk et al. | 433/226 |
| 5,169,318 | 12/1992 | Levy | 433/226 |
| 5,171,150 | 12/1992 | Levy | 433/226 |
| 5,201,655 | 4/1993 | Friedman | 433/29 |
| 5,334,016 | 8/1994 | Goldsmith et al. | 433/29 |
| 5,382,163 | 1/1995 | Putnam | 433/29 |
| 5,397,892 | 3/1995 | Abdelqader | 433/29 |
| 5,634,711 | * 6/1997 | Kennedy et al. | 433/29 |
| 5,912,470 | * 6/1999 | Eibofner et al. | 433/29 |
| 5,922,605 | * 7/1999 | Feurstein et al. | 433/29 |
| 6,095,812 | * 8/2000 | Senn et al. | 433/29 |
| 6,103,203 | * 8/2000 | Fischer | 433/29 |

FOREIGN PATENT DOCUMENTS

| | | | |
|---|---|---|---|
| 3436830 | 4/1986 | (DE) | 433/29 |
| 2028994 | 3/1980 | (GB) | 433/29 |
| 2122860 | 1/1984 | (GB) | 433/29 |
| 03104 | 3/1992 | (WO) | 433/29 |

\* cited by examiner

*Primary Examiner*—Stephen R. Funk
(74) *Attorney, Agent, or Firm*—Gifford, Krass, Groh, Sprinkle, Anderson & Citkowski, P.C.

(57) ABSTRACT

A curing system for a photohardenable material is disclosed having an electrically powered light source and a variable power supply electrically connected to the light source. During calibration, a photocell determines the power output of the light source and produces an output signal representative thereof. A control circuit then controls the illumination of the light source by the power supply. This control circuit includes a comparator which compares the power output signal from the photocell with a target value and then varies or increases the power from the power supply to the light source up to a maximum power output whenever the power output signal from the photocell is less than the target value. Following calibration, the control circuit also activates the power supply for a time period sufficient to obtain a substantially constant energy output from the light source per light activation. In the event that the power output signal is less than the target value and also that the power supply is at its maximum power output, the control circuit increases the duration of illumination of the light source beyond a preset time period by an amount sufficient to obtain a substantially constant energy output from the light source per activation.

6 Claims, 1 Drawing Sheet

CURING SYSTEM FOR PHOTOHARDENABLE MATERIALS

CROSS REFERENCE TO RELATED APPLICATIONS

This application is a continuation-in-part of patent application Ser. No. 08/285,907, filed Aug. 4, 1994, entitled "Curing System for Photohardenable Materials."

BACKGROUND OF THE INVENTION

I. Field of the Invention

The present invention relates to a curing system for photohardenable materials of the type used in dental restoration work.

II. Description of the Prior Art

In dentistry, it is oftentimes necessary to restore certain portions of the patient's teeth. For example, such restoration may be required after removal of a cavity from the patient's teeth.

Although gold, amalgam and other metals have been used for such restoration work in the past, in many situations it is more desirable to use a photohardenable material. Such photohardenable materials have a whitish color designed to match the patient's teeth. Thus, once the photohardenable material has been placed on the affected area of the patient's teeth and cured, the restoration becomes invisible or almost invisible, and is thus aesthetically more pleasing than the previously known use of gold and/or amalgam.

There have been two previously known types of light sources used to cure photohardenable materials of the type used in dental restoration work. Specifically, argon lasers have been used to cure such photohardenable materials in a very rapid time, typically in the range of 5 to 10 seconds. The primary disadvantage of argon lasers, however, is that they are very costly to obtain.

Because of the high cost of argon lasers, incandescent lights, such as halogen lights, have also been used as a light source in order to cure the photohardenable materials in dental applications. Such lights are advantageous over the previously known argon lasers since halogen lights cost in the range of 5–10% of the cost of a comparative argon laser.

A still further disadvantage of the use of halogen lights is that such lights degradate over a period of time. Once the power output from the light decreases, less energy, i.e. power integrated over time, from the light is obtained. Since photohardenable materials require a minimum amount of energy in order to obtain a full cure, the use of an incandescent light for an insufficient time period may result in an inadequate cure of the photohardenable material.

SUMMARY OF THE PRESENT INVENTION

The present invention provides a curing system for photohardenable materials of the type used in dental restorations which overcomes all of the above-mentioned disadvantages of the previously known devices.

In brief, the curing system of the present invention comprises an electrically powered light source which is preferably a xenon bulb or xenon arc light although other types of light sources may alternatively be used. A variable power supply is electrically connected to the light source so that, upon activation of the system, the power supply illuminates the light source. Furthermore, the power output from the light source varies as a function of the power output from the power supply and through the light source. For example, in the case of an incandescent light such as a halogen light, the voltage across the light is varied to vary the power output. Conversely, for a xenon arc light, the current is varied to vary the power output from the light.

During calibration, means, such as a photocell, are provided for determining the power output of the light source and for producing a power output signal representative thereof This power output signal is coupled as an input signal to a microprocessor or other electronic control circuit which then compares the power output signal from the photocell with a preset target value. If the power output from the light source is substantially the same as the target value, at least within predetermined thresholds, the microprocessor maintains a control signal for the power supply at its current level, and thus illumination of the light source, for a preset time period sufficient to provide enough energy to the photohardenable material to effect a complete cure of the photohardenable material.

Conversely, in the event that the power output signal from the photocell is less than the target value, the microprocessor varies the control signal to the power supply by an amount to increase the power output of the power supply and thus the power output of the light source. The microprocessor iteratively increases the power output from the power supply to the light source until either (1) the target value for the power output from the light source has been achieved or (2) the maximum power output from the power supply has been reached.

In the latter case, the microprocessor extends the duration of activation of the power supply, and thus extends the illumination of the light source, by an amount sufficient to achieve a predetermined amount of light energy from the light source. This predetermined amount of light energy is sufficient to completely cure the photohardenable material.

In the preferred embodiment, the microprocessor utilizes a lookup table stored in digital memory to determine the new time period for activation of the light source as a function of the power output signal from the photocell whenever the power supply is at its maximum current rating. The microprocessor also preferably outputs a signal to a display, such as an LED or a LCD display, representative of the time period required for complete cure of the photohardenable material. Such a display is helpful to the dentist to determine when it is economically desirable to replace the light source and thus reduce the cure time for the photohardenable material.

BRIEF DESCRIPTION OF THE DRAWINGS

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
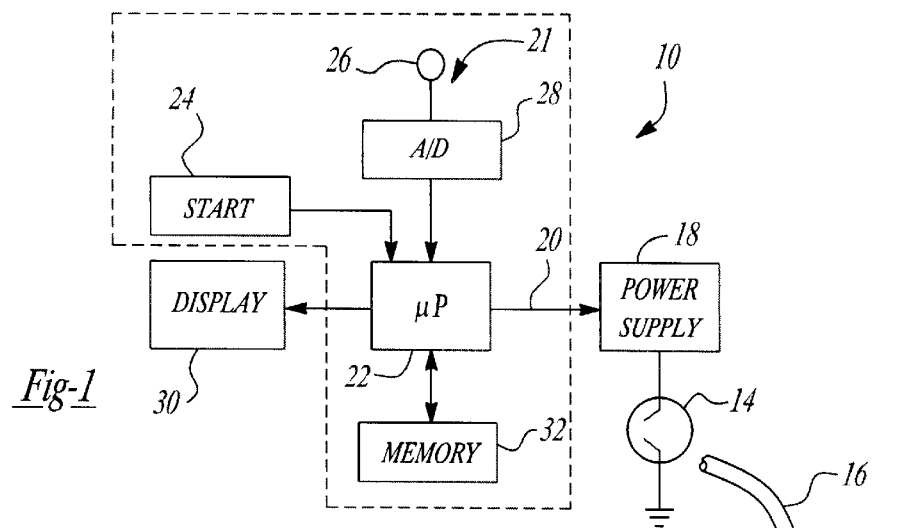
FIG. 1 is a block diagrammatic view illustrating a preferred embodiment of the present invention.

With reference first to FIG. 1, a block diagrammatic view of the curing system 10 of the present invention is there shown. The curing system 10 includes a light source 14. Preferably, the light source 14 is a xenon arc light although other types of lights, such as a halogen light, may alternatively be used. Furthermore, any conventional delivery system, such as a fiberoptic 16, can be used to deliver the light output from the light source 14 to a target site.

A variable power output power supply 18 is electrically connected to the light source 14 so that, upon activation of the system 10, the power supply 18 provides electrical power to the light source 14 thus illuminating the light source 14. The power supply 18 is capable of providing a variable power up to a preset maximum amount in dependence upon a control signal on an input line 20 to the power supply 18. Typically, the power output from the power supply 18 varies as a function of the voltage value on its input line 20. Furthermore, the power supply 18 may be a variable current or variable voltage power supply depending upon the type of light source 14.

A control circuit 21 having a microprocessor 22 or other electronic control means, is electrically connected to the power supply input 20 such that the microprocessor 22 controls not only the activation of the power supply 18, but also the power output of the power supply 18. The microprocessor 22 receives an input signal from a start switch 24, such as a foot pedal or other switch, in order to initiate the activation of the system 10 and thus the illumination of the light source 14. The microprocessor 22 preferably activates the system 10 by activating the power supply but, alternatively, may activate electronic switch(es) electrically connected between the power supply 18 and light source 14.

In order to calibrate the system 10, a photocell or other light detector 26 is also electrically connected to the control circuit 21 through an analog/digital converter 28. Thus, the output from the photocell 26 as well as the value of the signal from the A/D converter 28, is representative of the instantaneous light power of light impinging on the photocell 26 during a calibration test. This power output signal is coupled as an input signal to the microprocessor 22.

The microprocessor 22 also controls the operation of a display 30 which displays the time of activation of the light source 14 in a fashion which will be subsequently described. Furthermore, the microprocessor 22 preferably is electrically connected and/or contains digital memory 32. This digital memory 32 contains not only the program necessary to control the operation of the microprocessor 22, but also controls data which varies the operation of the photocuring system 10.

Figure 2:
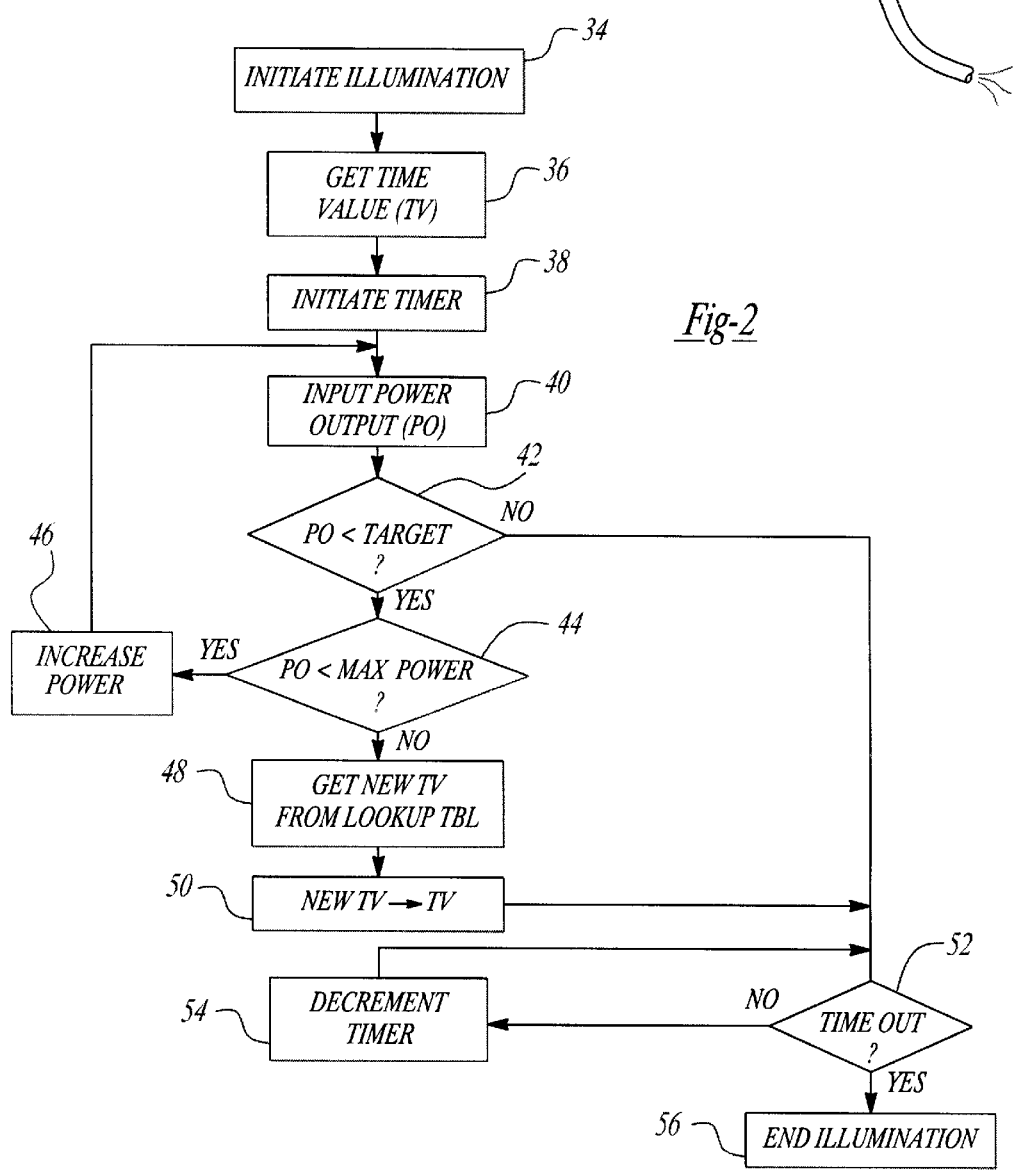
FIG. 2 is a flow chart illustrating the operation of the preferred embodiment of the present invention.

With reference now to FIG. 2, the operation of the calibration program for the system 10 is there shown. At step 34 and with the light output from the light source 14 directed towards the photocell 26, the microprocessor 22 in the control circuit 21 receives a signal from the start switch 24 and initiates the illumination of the light source 14. Step 34 then branches to step 36.

At step 36, the microprocessor 22 obtains the time value Tv from memory 32 which is representative of the time duration of illumination of the light source 14 necessary to obtain sufficient energy from the light source 14 to effect a complete cure of the photohardenable material. Step 36 then branches to step 38 where the control circuit 22 initiates a timer representative of a duration of the cure time necessary to effect a complete cure of the photohardenable material. Step 38 then branches to step 40.

At step 40, the control means 22 inputs a power output signal from the photocell 26 as an input signal. Preferably, in order to obtain this output signal, the light delivery means 16 has its outlet end positioned in registry with the photocell 26 such that the light output from the delivery system 16 impinges on the photocell 26. Step 40 then branches to step 42. At step 42, the program compares the power output signal (PO) with a target value to determine if the power output from the light delivery system 16 is within preset tolerances of the target value. If the power output is less than the target value, step 42 branches to step 44.

At step 44, the program determines if the power from the power supply 18 is less than its maximum value. If so, step 44 branches to step 46 where the microprocessor 22 generates an output signal to the power supply input 20 to increase the power output from the power supply 18 and thus increase the illumination power of the light source 14. For example, in the case of a xenon arc light, the current from the power supply 18 is increased while for incandescent bulbs, the voltage is increased. Step 46 then branches back to step 40 where the above process is iteratively repeated until the power output from the light source 14 achieves the target value at step 42.

Conversely, if the power output from the power source 18 is at its maximum value, step 44 instead branches to step 48 in which the control circuit 22 obtains a new time value Tv from a lookup table stored in the digital memory 32. The lookup table is designed so that the new value Tv which varies as a function of the power output from the light source 14 is such that the total energy, i.e. power integrated over time, that is delivered by the light source 14 is substantially constant and sufficient to achieve complete curing of the photohardenable material. This new value Tv is then stored in the digital memory 32 at step 50. Step 50 then branches to step 52 and, likewise, step 42 also branches to step 52 in the event that the power output from the light source achieves the target value. Step 52 and step 54 form a timing loop which decrements the timer, i.e. the value Tv, until the time reaches a zero value. At that time, step 52 branches to step 56 in which the microprocessor 22 generates an output signal to the power supply 18 to terminate the activation of the power supply 18 and thus illumination of the light source 14.

Consequently, it can be seen that the curing system of the present invention incrementally increases the electrical power to the light source in order to maintain the power or light output from the light source 14 at a preset target value. As long as the power output from the light source achieves the target value, the curing system activates the power supply and thus illuminates the light source for a predetermined time period, e.g. ten seconds in the case of a xenon bulb.

Conversely, whenever the power supply 18 output is at its maximum power output, the curing system 10 of the present invention then increases the duration of the illumination of the light source during each system activation in an amount sufficient to deliver substantially the same amount of energy from the light source. At this time, the microprocessor 22 also generates an output signal to the display 30 indicative of the time duration of the light source per activation. As the light source continues to degrade and the duration of activation increases as shown on the display 30, at some point it becomes economically more desirable to replace the light source 14 thus reducing the required illumination time of the light source 14 in order to achieve complete curing of the photohardenable material.

From the foregoing, it can be seen that the curing system of the present invention provides a simple and yet completely effective means for insuring that the same amount or substantially the same amount of energy is provided by the light source during each activation of the curing system. Having described my invention, however, many modifications thereto will become apparent to those skilled in the art to which it pertains without deviation from the spirit of the invention as defined by the scope of the appended claims.

I claim:

1. A curing system for a photohardenable material comprising:

an electrically powered light source, a variable power output power supply electrically connected to said light source, means for determining a power output of said light source and for producing a power output signal representative thereof, means for controlling illumination of said light source by said power supply per system activation, said control means comprising:

means for comparing said power output signal with a target value and for varying the power output up to a maximum power amount from said power supply to said light source whenever said power output signal varies from said target value, means for illuminating said light source from said power supply for a time period sufficient to obtain a substantially constant energy output from said light source, means for activating said power supply for a preset time period whenever the power supply power output is less than said maximum power amount so that the energy output from said light source per activation of said power supply is substantially constant, and a time adjustment means operable when said power supply output is substantially at said maximum power amount and when said power output signal is less than said target value for increasing the duration of activation said power supply longer than said preset time period by an amount sufficient to obtain a substantially constant energy output from said light source per activation of the curing system.

2. The curing system as defined in claim 1 wherein said light source is a xenon arc light.

3. The curing system as defined in claim 1 wherein said control means comprises a programmed microprocessor.

4. The curing system as defined in claim 1 wherein said control means comprises a microprocessor and digital memory connected to said microprocessor, and wherein said time adjustment means includes a lookup table stored in the digital memory.

5. The curing system as defined in claim 1 wherein said power output determining means comprises a photocell having an output signal which varies as a function of light power input.

6. The curing system as defined in claim 1 and comprising a display electrically connected to said control means, said control means generating an output signal to said display indicative of the time duration for each activation of said light source.

* * * * *